United States Patent [19]

Tie et al.

[11] Patent Number: 4,850,995
[45] Date of Patent: Jul. 25, 1989

[54] CENTRIFUGAL SEPARATION OF BLOOD

[75] Inventors: Thomas K. Tie, Concord, Calif.; Mark A. Holmes, Conifer; Anne W. Rank, Golden, both of Colo.

[73] Assignee: Cobe Laboratories, Inc., Lakewood, Colo.

[21] Appl. No.: 87,162

[22] Filed: Aug. 19, 1987

[51] Int. Cl.[4] .............................................. A61N 1/36
[52] U.S. Cl. ......................................... 604/6; 494/37
[58] Field of Search .................. 604/5, 6, 410; 494/35, 494/37, 45, 18

[56] References Cited

U.S. PATENT DOCUMENTS

| | | | |
|---|---|---|---|
| 2,869,779 | 1/1959 | Geissler | 494/35 X |
| 3,849,145 | 1/1970 | Judson et al. | 604/6 |
| 4,094,461 | 6/1978 | Kellog et al. | 494/45 |
| 4,185,629 | 1/1980 | Cullis | 604/6 |
| 4,464,167 | 8/1984 | Schoendorfer et al. | 604/6 |

OTHER PUBLICATIONS

"Cobe 2997 Blood Cell Separator Operator's Handbook", c. 1985, Cobe Labs, Inc., Lakewood, CO.
"CS-3000 Blood Cell Separator Operator's Manual", c. 1983, Fenwal Labs, Div. of Travenol Labs, Deerfield, IL.

Primary Examiner—Martin P. Schwadron
Assistant Examiner—Allen J. Flanigan

[57] ABSTRACT

Returning red blood cells to a patient after a centrifuge separation procedure by connecting an inflow line of a separation channel to an outflow line to provide a closed loop and recirculating liquid through it to remove blood cells. Also disclosed is pulling more liquid out of a flexible separation channel than permitted into it in order to reduce the volume of liquid to be used in returning cells to the patient.

11 Claims, 2 Drawing Sheets

| ELEMENT OR PARAMETER | STEP 1 (COLLECTING) | STEP 2 (RETURN RBC) | STEP 3 (RECIRCULATING FREE CELLS) | STEP 4 (RETURN RBC COLLAPSE CHAN.) | STEP 5 FINAL RINSE | STEP 6 (COMPLETE) |
|---|---|---|---|---|---|---|
| AC PUMP 30 | STOPPED | STOPPED | STOPPED | STOPPED | STOPPED | |
| INLET PUMP 32 | ___ ML/MIN | 500 ML/MIN | STOPPED | STOPPED | 500 ML/MIN | |
| PLASMA PUMP 34 | ___ ML/MIN | STOPPED | 1500 ML/MIN | 500 ML/MIN | 500 ML/MIN | |
| COLLECT PUMP 36 | ___ ML/MIN | STOPPED | 500 ML/MIN | 0.0 ML/MIN | 0.0 ML/MIN | STOPPED |
| CENTRIFUGE | ___ RPM | STOPPED | STOPPED | STOPPED | STOPPED | STOPPED |
| WASTE VALVE 38 | CLOSED | CLOSED | RECIRCULATE POSITION | CLOSED | CLOSED | CLOSED |
| PLASMA VALVE 40 | VARIABLE POSITION | RETURN POSITION | RETURN POSITION | RETURN POSITION | RETURN POSITION | RETURN POSITION |
| COLLECT VALVE 42 | COLLECT POSITION | RETURN POSITION | RETURN POSITION | RETURN POSITION | RETURN POSITION | RETURN POSITION |
| RBC LINE VALVE 44 | OPEN | OPEN | CLOSED | CLOSED | CLOSED | OPEN |
| RETURN LINE VALVE 38 | OPEN | OPEN | CLOSED | OPEN | OPEN | CLOSED |
| APPROXIMATE VOLUME | 60 ML INLET | 90 ML/MIN | 225 ML PLASMA | 125 ML PLASMA | 58 ML INLET | |
| APPROXIMATE TIME | | 108 SECONDS | 90 SECONDS | 150 SECONDS | 70 SECONDS | |

OPERATOR: CLAMP & DISCONNECT ACCESS. OPEN ACCESS SALINE. PRESS CONTINUE TO RINSEBACK.

OPERATOR: CLAMP & DISCONNECT COLLECTION BAGS. PRESS CLEAR.

OPERATOR: DISCONNECT RETURN LINE. CLOSE FLUIDS. PRESS CONTINUE.

FIG. 2

CENTRIFUGAL SEPARATION OF BLOOD

FIELD OF THE INVENTION

The invention relates to centrifugal separation of blood.

BACKGROUND OF THE INVENTION

Centrifugal separators used in continuously separating blood components can employ a disposable plastic channel that is fitted within a centrifuge bowl that is rotatably driven by a motor. The channels typically have an inlet for whole blood and two or more outlets at different radial locations to remove separated fractions of blood components in the channels, plasma being at the most radially inward location and red blood cells being at the most radially outward location. In various component collection or exchange procedures the red blood cells are usually returned to the patient/donor along with some other components during the continuous separation procedure.

At the end of a separation procedure, it is desirable to remove the red blood cells remaining in the channel and to return them to the patient/donor. In one prior art centrifuge system involving a plastic separation channel of the general type disclosed in Kellogg et al. U.S. Pat. No. 4,094,461, at the end of a run saline is connected to the input line. A pinch valve blocks the input line while a pump pulls on an output line to cause the channel to collapse, and the pinch valve then unblocks the input line, causing saline to quickly enter the channel and to flush red blood cells out.

SUMMARY OF THE INVENTION

In one aspect the invention features in general removing blood cells from a channel for return to a patient/donor after a centrifuge separation procedure by connecting an outflow line to an inflow line and recirculating liquid through the channel. By using recirculation, the dilution of cells being returned to the patient is reduced at the same time that the total volume flowing past a given location in the channel in order to free cells is increased.

In another aspect the invention features in general collapsing a centrifuge channel by pulling more liquid out of the channel with an outflow pump than is permitted into the channel, thereby reducing the volume of liquid to be used in returning blood cells to the patient/donor.

In preferred embodiments both recirculation and channel collapsing are employed; prior to recirculation the patient is disconnected from the inflow line, and saline solution is pumped into the extracorporeal circuit while the centrifuge continues to separate and collect blood components; a red cell outflow line from the channel is flushed out, and is then blocked during the recirculation step to prevent short circuiting; the channel is collapsed by blocking inflow and then rinsed while maintained in a collapsed condition by keeping the inflow and outflow of liquid to and from the channel substantially equal.

Other features and advantages of the invention will be apparent from the following description of a preferred embodiment thereof and from the claims.

DESCRIPTION OF THE PREFERRED EMBODIMENT

The preferred embodiment will now be described.

DRAWINGS

FIG. 2 is a chart describing an automatic method of returning red blood cells to a patient/donor at the end of a separation procedure using the FIG. 1 system.

STRUCTURE

Figure 1:
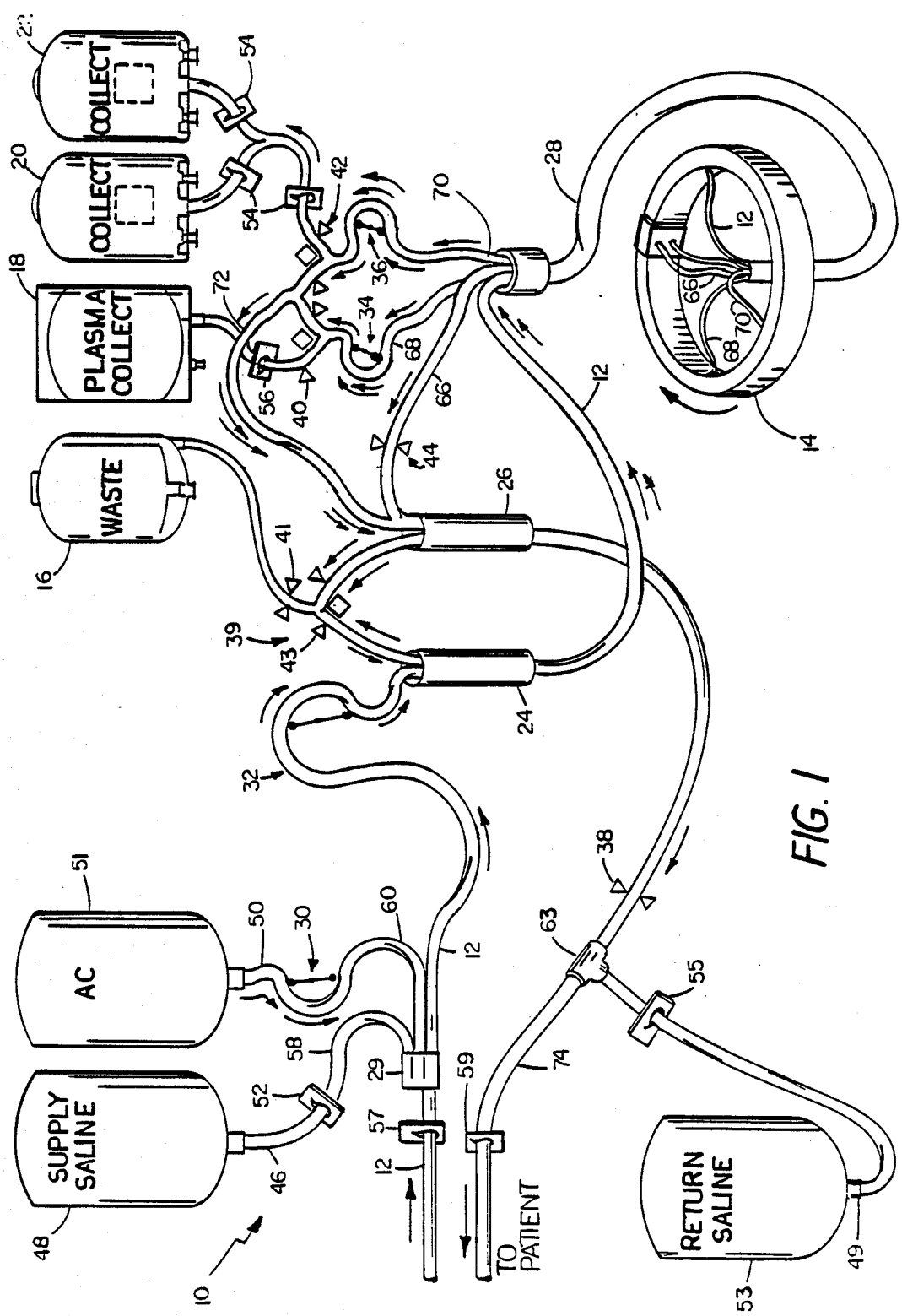
FIG. 1 is a hydraulic schematic of a centrifugal blood separating system according to the invention.

Referring to FIG. 1, there is shown blood centrifugal separating system 10, used to continuously separate components in blood removed from a patient via inflow line 12. Separation is in disposable plastic separation channel 14, which is mounted in a bowl (not shown) and rotated.

Blood inflow line 12 and disposable channel 14 are part of a disposable tubing set including waste collect bag 16, plasma collect bag 18, platelet collect bags 20, 22, inflow and return air chambers 24, 26, and seal-less multichannel rotation connection assembly 28 (e.g., as shown in U.S. Pat. No. 4,146,172). The disposable tubing set is mounted on the front surface of a machine having peristaltic pump rollers to provide, with the tubing, anticoagulant pump 30, inlet pump 32, plasma pump 34, and collect pump 36, and pinch valve assemblies to provide, with the tubing, two-position return line valve 38, three-position plasma valve 40, three-position collect valve 42, two-position red blood cell line valve 44, and waste/divert valve assembly 39, including two-position waste valve 41, and three-position divert valve 43. The tubing set also includes filter/connector 46, for connecting separately supplied bag of saline 48, filter/connector 50, for connecting separately supplied bag of anticoagulant 51, and connector 49, for connecting return saline bag 53. The tubing set also includes manually-activated pinch clamps, namely saline supply clamp 52, collect clamps 54, plasma collect clamp 56, saline return clamp 55, and patient access supply and return clamps 57, 59. (Some of the manually-activated pinch clamps have structures that do not employ the decreasing width slots shown for all clamps in FIG. 1.)

Inflow line 12 joins saline supply line 58 and anticoagulant supply line 60 from pump 30 at four-way junction 29. From junction 29 inflow line 12 passes through inlet pump 32 and into inflow air chamber 24. From there inflow line 12 continues to seal-less connection assembly 28.

Disposable plastic channel 14 is a two-stage channel of the type described in more detail in U.S. Patent application Ser. No. 845,847. Other disposable plastic channels, for example, the type shown in the Kellogg patent mentioned above, can also be used.

The outflow lines from channel 14 include red blood cell return line 66, plasma line 68, and platelet collect line 70. Red blood cell line 66 is directly connected to return drip chamber 26. Plasma line 68 and platelet collect line 70 pass through their respective pumps 34, 36 and branch into two lines each, which pass through three-position valves 40, 42. Three-position plasma valve 40 can be operated to permit flow to plasma collect bag 18 (collect position), to return line 72 (return position), or to both (variable position). Three-position collect valve 42 can similarly permit flow to bags 20, 22 (collect position), to return line 72 (return position), or to both (variable position). Three-position divert valve 43 can similarly permit flow in either or both of its lines, and two-position valve 41 can permit or block flow through it to waste bag 16.

Return saline bag 53 is connected to return line 74 at a three-way junction 63.

OPERATION

In operation, the tubing set shown in FIG. 1 is installed on the machine and connected to saline bag 48, anticoagulant bag 51, and return saline bag 53. Saline solution is pumped into the tubing set to prime it. The venipuncture needles connected to inflow line 12 and return line 74 are inserted in the patient/donor, and supply pinch clamp 57 is opened, permitting removal of blood from the patient/donor, while return pinch clamp 59 initially remains closed. The collection procedure begins, the pumps operating to supply whole blood to channel 14 via inflow line 12 and to remove the separated red blood cells in line 66, plasma in line 68, and platelets in line 70. During the initial operation, the saline in the tubing set is displaced by the incoming blood and separated blood components and is diverted at return air chamber 26 for collection in waste bag 16. Valve 41 is used to permit removal of saline to waste bag 16 at the beginning of a donor/patient procedure, and to remove air from chambers 24, 26, when needed. When the separated red blood cells and plasma reach junction 63, waste/divert valve assembly 39 is closed (by blocking both pinch valves of valve 43 or by blocking either pinch valve of valve 43 and pinch valve 41) and return valve 38 is opened. The red blood cells and plasma are returned to the patient via line 74, and platelets are collected in bags 20, 22. During the collection procedure three-position collect valve 42 blocks flow to return line 72 and permits flow to collect bags 20, 22, and plasma return valve 40 permits flow to return line 72 and blocks flow to plasma collect bag 18. The flow through the tubing set during the collection procedure is as indicated by solid arrows in FIG. 1.

At the end of a collection procedure, the method described in FIG. 2 is employed to return red blood cells to the patient. First, prior to Step 1, the operator closes supply clamp 57, disconnects the venipuncture needle connected to the inflow line 12, and opens pinch valve 52 to provide access to supply saline in bag 48. The operator then returns the system to the automatic mode by activating a CONTINUE control. Anticoagulant pump 30 is stopped, as indicated in the listing for Step 1, and the other pumps operate (at desired flowrates) and the valves maintain their conditions, permitting continued collection of platelets for a few minutes while 60 ml saline flows through inflow tube 12, and drop chamber 24 (approximately 10-15 ml volume) and into channel 14 (approximately 160 ml volume). At this point the operator clamps and disconnects collection bags 20, 22 and returns to the automatic mode by activating the CLEAR control.

In Step 2, the centrifuge is stopped, causing an immediate breakdown in the layers in channel 14; this results in some of the red blood cells mixing with the separated plasma and saline in channel 14 and some remaining compacted at the outer wall of channel 14, primarily in the first stage region between the inlet and the red blood cell outlet. Inlet pump 32 is operated while plasma and collect pumps 34, 36 are stopped, causing all flow from channel 14 to be through red blood cell line 66. This causes the red blood cells in line 66 along with approximately 90 ml of the volume of channel 14 to be flushed through line 66 (which has very little volume) and return air chamber 26 into return line 74, about 10-15 ml remaining in return air chamber 26. Although line 66 has little volume, during operation it is packed with a very high density of red blood cells. During Step 3 the flow in channel 14 is substantially short circuited along the short flow path from the inlet to the red cell outlet, the region between these two including the majority of the red blood cells. At the end of Step 2, the liquid in line 66 has a much lower concentration of red blood cells. The 90 ml volume is chosen to substantially remove all free red blood cells from channel 14.

In Step 3, red blood cell line valve 44 and return line valve 38 are closed; plasma and collect valves 40, 42 are in the return position (so that all liquid through them goes to return line 72), and waste valve 39 is placed in the recirculate position with two-position valve 41 closed and three-position valve 43 open, causing the liquid to take the recirculating flow path shown by dashed arrows on FIG. 1. Thus liquid flows from inlet air chamber 24 through line 12 into and through channel 14, and from channel 14 the liquid goes through lines 68, 70, pumps 34, 36, and return line 72 to return air chamber 26. From there the liquid goes through three-position divert valve 43 and returns to drip chamber 24. If red blood cell line valve 44 were not closed, there would be short circuiting of the liquid through it. There is no flow to or from the patient/donor during this step. During Step 3, the red blood cells are flushed off the channel wall by recirculating liquid through channel 14 at a high flowrate of 200 ml per minute for 90 seconds. There is approximately 225 ml in the closed circuit, causing the liquid to be recirculated through the path approximately 1.33 times. Of the 225 ml closed loop volume, approximately 100 ml or more is saline solution.

In Step 4, waste valve 39 is moved to the closed position, and return valve 38 is opened, permitting return of plasma, freed red blood cells, and mixed saline to the patient/donor. Because inlet pump 32 is stopped, and plasma pump 34 is operated, channel 14 is collapsed, reducing its 160 ml volume by about 125 ml to about 35 ml.

In Step 5, inlet pump 32 is operated at 50 ml per minute, and plasma pump 34 is operated at 50 ml per minute, matching the inflow but maintaining the collapsed state of channel 14. More freed red blood cells are returned to the patient, with plasma and mixed saline. A volume of 58 ml is returned in this step, because after this amount has been returned the liquid is predominantly saline.

The operator disconnects the return line to the patient/donor. In Step 6, return valve 38 is automatically closed.

OTHER EMBODIMENTS

Other embodiments of the invention are within the scope of the following claims. For example, the collecting step need (Step 1) not be used, the 60 ml volume being added to the 90 ml volume of the Step 2.

What is claimed is:

1. A method of returning blood cells to a patient/donor after a centrifuge separation procedure comprising
providing centrifuge apparatus including a separation channel for separating blood components and an inflow line to and outflow lines from said channel, ending a centrifuge separation procedure by stopping rotation of said separation channel, connecting said inflow line to a said outflow line to provide a closed loop, and recirculating liquid through said channel to free and suspend blood cells in said channel while said channel is not rotating.

2. The method of claim 1 wherein an outflow line is a red blood cell line for removing red blood cells, and further comprising, prior to said connecting, flushing said red blood cell line to remove red blood cells therein, and thereafter blocking said red blood cell line, and wherein during said recirculating said red blood cell line is maintained blocked.

3. The method of claim 2, further comprising, prior to said flushing, disconnecting said inflow line from said patient/donor and connecting a supply saline solution to said inflow line, and wherein, after said connecting and prior to said flushing, components separated in said channel are collected.

4. The method of returning blood cells to a patient/donor after a centrifuge separation procedure comprising providing centrifuge apparatus including a flexible separation channel for separating blood components and an inflow line to and outflow lines from said channel, and pulling more liquid out of said channel with an outflow pump than is permitted into said channel in order to substantially collapse said channel to reduce the volume of liquid to be used in returning cells to said patient/donor, and rinsing liquid through said channel while maintaining said channel collapsed to flush blood cells from said channel while using a decreased volume of liquid owing to the decreased volume of said channel.

5. The method of claim 4 wherein inflow to said channel is blocked during said pulling to substantially collapse said channel.

6. The method of claim 5 wherein an outflow line is a red blood cell line for removing red blood cells, and further comprising, prior to said pulling, flushing said red blood cell line to remove red blood cells therein, and thereafter blocking said red blood cell line, and wherein during said pulling said red blood cell line is maintained blocked.

7. The method of claim 5, further comprising, prior to said flushing, disconnecting said inflow line from said patient/donor and connecting a supply saline solution to said inflow line, and wherein, after said connecting and prior to said flushing, components separated in said channel are collected.

8. The method of claim 1 wherein said channel is flexible, and further comprising, after said recirculating, pulling more liquid out of said channel with an outflow pump than is permitted into said channel in order to reduce the volume of liquid to be used in returning cells to said patient/donor.

9. The method of claim 8 wherein inflow to said channel is blocked during said pulling to substantially collapse said channel, and further comprising thereafter rinsing liquid through said channel while maintaining said channel collapsed to flush blood cells from said channel while using a decreased volume of liquid owing to the decreased volume of said channel.

10. The method of claim 1 wherein said apparatus includes an inflow line drip chamber and a return line drip chamber that both have waste lines joined at a waste junction, and wherein said connecting includes operating said valve to cause liquid to be able to flow from said return line drip chamber to said inflow line drip chamber via said waste lines.

11. The method of claim 1 wherein said outflow lines include a plasma outlet line and a platelet collect outlet line, said plasma outlet line and said platelet collect outlet line each branching into two lines, one each connected to a collection bag and one each joined at a return junction connected to a return line to said patient/donor, and wherein said apparatus includes valves controlling flow through said two lines, and wherein said connecting includes operating said valves to cause liquid to be able to flow through said return junction.

* * * * *